US 7,434,457 B2

(12) United States Patent
Goodwin et al.

(10) Patent No.: US 7,434,457 B2
(45) Date of Patent: Oct. 14, 2008

(54) FLUID PROPERTY SENSORS

(75) Inventors: Anthony Goodwin, Thomaston, CT (US); Eric Donzier, Brookfield, CT (US); Maria Manrique, Cambridge (GB); Sarah Pelham, Cambridge (GB); Gerry Meeten, Herts (GB)

(73) Assignee: Schlumberger Technology Corporation, Ridgefield, CT (US)

( * ) Notice: Subject to any disclaimer, the term of this patent is extended or adjusted under 35 U.S.C. 154(b) by 93 days.

(21) Appl. No.: 10/104,495

(22) Filed: Mar. 22, 2002

(65) Prior Publication Data
US 2002/0194906 A1 Dec. 26, 2002

Related U.S. Application Data

(60) Provisional application No. 60/286,293, filed on Apr. 26, 2001, provisional application No. 60/278,302, filed on Mar. 23, 2001.

(51) Int. Cl.
*E21B 44/00* (2006.01)

(52) U.S. Cl. ............... 73/152.46; 73/290 V; 73/290 R; 361/160

(58) Field of Classification Search ............... 73/290 R, 73/290 V, 152.46; 361/160, 159
See application file for complete search history.

(56) References Cited

U.S. PATENT DOCUMENTS

| 4,023,562 A * | 5/1977 | Hynecek et al. ............. 600/561 |
| 4,841,775 A | 6/1989 | Ikeda et al. .................... 73/704 |
| 5,009,108 A | 4/1991 | Harada et al. ................. 73/704 |
| 5,146,787 A | 9/1992 | Thomas et al. ................ 73/704 |
| 5,739,431 A | 4/1998 | Petri ............................ 73/509 |
| 6,044,705 A * | 4/2000 | Neukermans et al. .... 73/504.02 |
| 6,128,949 A | 10/2000 | Kleinberg ................. 73/152.18 |
| 6,230,557 B1 * | 5/2001 | Ciglenec et al. .......... 73/152.01 |
| 6,322,247 B1 * | 11/2001 | Bonne et al. ................. 374/138 |
| 6,361,206 B1 * | 3/2002 | Bonne ........................ 374/138 |

FOREIGN PATENT DOCUMENTS

| EP | 0 978 630 A2 | 2/2000 |
| GB | 2 201 776 A | 9/1988 |

(Continued)

OTHER PUBLICATIONS

Burger et al., "Miniaturized Friction Force Measuring System for Tribological Research on Magnetic Storage Devices", Nov. 2, 1996, IEEE, Table 2, p. 102.*

(Continued)

*Primary Examiner*—Hezron E. Williams
*Assistant Examiner*—Rodney T Frank
(74) *Attorney, Agent, or Firm*—William B. Batzer; Jody Lynn DeStefanis; James McAleenan

(57) ABSTRACT

Micro-Electro Mechanical Systems (MEMS) based fluid sensors adapted to measure physical properties of oilfield reservoir fluids under downhole conditions. Certain embodiments of the invention may be characterized as a MEMS based reservoir fluid sensor adapted for downhole conditions having a planar member machined from a substrate material, an electrical conductor formed at least partly on the planar member; and a gauge formed on the planar member and adapted to measure a physical effect on the planar member, the physical effect being indicative of a property of a fluid in contact with the planar member.

30 Claims, 7 Drawing Sheets

FOREIGN PATENT DOCUMENTS

| | | |
|---|---|---|
| GB | 2348222 A | 9/2000 |
| WO | WO 98/45691 | 10/1998 |
| WO | WO 99/66172 | 12/1999 |
| WO | WO 00/66266 | 11/2000 |

OTHER PUBLICATIONS

Daikhin, L. et al. Influence of Surface Roughness on the Quartz Crystal Microbalance Response in Solution. *Faraday Discussions*, vol. 107 (1997) pp. 27-38.

Happel, J. et al. Low Reynolds Number Hydrodynamics. *Kluwer Academic Publishers*. (1991) p. 215.

Landau, L. D. et al. *Theory of Elasticity—Course of Theoretical Physics, vol. 7.* Pergamon Press (1986) Chapter III—Elastic Waves. pp. 87-107.

Landau, L. D. et al. Fluid Mechanics Course of Theoretical Physics, vol. 6. *Pergamon Press* (1987) pp. 83-92.

Lindholm, U.S. et al. Elastic Vibration Characteristics of Cantilever Plates in Water. *J. Ship Res.* vol. 9 (1965) pp. 11-36.

Sader, J. E. Frequency Response of Cantilever Beams Immersed in Viscous Fluids with Applications to the Atomic Force Microscope. *J. Applied Phys.*, vol. 84, (1998). pp. 64-76.

Donzier, E. et al. "Integrated Magnetic Field Sensor". *Sensors and Actuators A*, 25-25 (1991), pp. 357-361.

Ahmed, Nabil et al. Measurements of solution viscosity by atomic force microscopy. *Rev Sci. Instrum* V72, No. 6. (Jun. 2001) pp. 2731-2734.

Ambrose, D. and Walton, J. Vapour pressures up to their critical temperatures of normal alkanes and 1-alkanols. *Pure & Appl. Chem.* V 61, No. 8. (1989) pp. 1395-1403.

Andrews, M.K and Harris, P.D. Damping and a gas viscosity measurements using a micostructure. *Senssors and Actuators A*, V49. (1995) pp. 103 108.

Assael, M. J et al. Correlation and Prediction of Dense Fluid Transport Coefficients. I. n-Alkanes. *Int. J. Thermophys.*, V13, No. 2 (1992) pp. 269-281.

Baker, Wilfred E. et al. Air and internal damping of thin cantilever beams. *Int. J. Mech. Sci.* V9, (1967) pp. 743-766.

Baller, M.K. et al. *A cantilever array-based artificial nose.* Ultramicroscopy. V82 (2000) pp. 1-9.

Banipal, T.S., et al. Heat capacities and densities of liquid n-octane, n-nonane, n-decane, and n-hexadecane at temperatures from 318.15 K to 373.15K and at pressures up to 10 MPa. *J. Chem. Thermodyn.* V23 (1991) pp. 923-931.

Battiston, F.M. et al. A chemical based on a microfabricated cantilever array with simultaneous resonance-frequency and bending readout. *Sens. Actuators B*, V77 (2001) pp. 122-131.

Belonenko V.N., et al. Application of a Micro-(p, V, T) apparatus for measurement of liquid densities at pressures up to 500 MPa. *J. Chem Thermodyn.* V32, (2000) pp. 1203-1219.

Bergaud, C. and Nicu, L. Viscosity measurements based on experimental investigations of composite cantilever beam eigenfrequencies in viscous media. *Rev. Sci. Instrum.* V71, No. 6 (Jun. 2000) pp. 2487-2491.

Binnig, G. et al., Atomic Force Microscope. *Phys. Rev. Lett.* V56, No. 9 (Mar. 3, 1986) pp. 930-933.

Bridgman, P.W. The Volume of Eighteen Liquids as a Function of Pressure and Temperature. *Proc. Am. Acad. Arts Sci.* V66, No. 5 (1931) pp. 185-233.

Chang, R. F. and Moldover, M. R. High-temperature high-pressure oscillating tube densimeter. *Rev. Sci. Instrum.* V67 No. 1 (1996) pp. 251-256.

Chang, T.-P. and Liu, M.-F. On the natural frequency of a rectangular isotropic plate in contact with fluid. *J. Sound Vib.* V 236 (2000) pp. 547-553.

Chen, G. Y. et al. Harmonic response of near-contact scanning force microscopy. *Rev. Sci. Instrum.*, V78, No. 3 (Aug. 1, 1995) pp. 2532-2537.

Chen, G.Y. et al. Resonance response of scanning force microscopy cantilevers. *J. Appl. Phys.* V65, No. 8 (1995) pp. 1465-1469.

Chon, James W.M. et al. Experimental validation of theoretical models for the frequency response of atomic force microscope cantilever beams immersed in fluids. *J. Appl. Phys.*, V87, No. 8 (Apr. 15, 2000) pp. 3978-3988.

Corman, Tierry et al. A low-pressure encapsulated resonant fluid density sensor with feedback control electronics. *Meas. Sci. Technol.* V11 (2000) pp. 205-211.

Cortez, Ricardo. The Method of Regularized Stokeslets, *SIAM J. Sci.Comput.* V.23, No. 4 (2001) pp. 1204-1225.

Cumberbatch, Ellis and Fitt, Alistair. Mathematical Modelling: case studies from industry, *Cambridge University Press*, Cambridge, U.K. (2001) pp. 66-79.

Cumberbatch, Ellis and Wilks, Graham. An analysis of a vibrating element densitometer, *Math. Engng. Ind.* V1, No. 1 (1987) pp. 47-66.

Dix, M. et al. A Vibrating-OWire Densimeter for Measurements in Fluids at High Pressures. *Int. J. Thermophys.*, V12, No. 2 (1991) pp. 357-370.

Donzier, E. et al. Integrated Magnetic Field Sensor. *Sens. Actuators A*. 25-27 (1991) pp. 357-361.

Dymond, J.H et al. Transport Properties of Nonelectrolyte Liquid Mixtures—III. Viscosity Coefficients for n-Octane, n-Dodecane, and Equimolar Mixtures of n-Octane + n-Dodecane and n-Hexane + n-Dodecane from 25 to 100° C. at Pressures Up to the Freezing Pressure or 500 MPa. *Int. J. Thermophys.* V2, No. 2 (1981) pp. 133-154.

Dymond, J.H. et al. Transport Properties of Nonelectrolye Liquid Mixtures. VIII. Viscosity Coefficients for Toluene and foir Three Mixtures of Toluene + Hexane from 25 to 100° C. at Pressures up to 500 MPa. *Int. J. Thermophys,* . V12, No. 2 (1991) pp. 275-287.

Elmer, Franz-Josef and Dreier, Markus. Eigenfrequencies of a rectangular atomic force microscope cantilever in a medium. *J. Appl. Phys.*, V81, No. 12(1997) pp. 7709-7714.

Enoksson, Peter et al. Fluid density sensor based on resonance vibration. *Sens. Actuators A.* 46-47 (1995) pp. 327-331.

Franck, E.U. et al. The Density of Toluene at High Pressures to 673 K and 300 MPa. *Ber. Bunsenges Phys. Chem.*, V102, No. 12 (1988) pp. 1794-1797.

Froba, A.P. and Leipertz, A. Viscosity and Surface Tension of Saturated Toluene from Surface Ligh Scattering (SLS). *Int. J. Thermophys.* V22, No. 1 (2001) pp. 41-59.

Godin, Michel. Quantitative surface stress measurements using a microcantilever. *Appl. Phys. Lett.* V79, No. 4 (2001) pp. 551-553.

Gouel, Patrick, Densities of Alcanes ($C_6$ to $C_{16}$) Cyclics and Alkyl-Benzenes. *Bull. Cent. Rech. Explor.-Prod. Elf-Aquitaine*, V2, No. 1 (1978) pp. 211-225.

Hagleitner, C. et al. Smart single-chip gas sensor microsystem. *Nature*, V414 (Nov. 15, 2001) pp. 293-296.

Hinch, E.J. Perturbation Methods, *Cambridge University Press*: Cambridge, U.K. (1991) pp. 87-90.

Judy, Jack W. Microelectromechanical system (MEMS): fabrication, design and applications. *Smart Mater. Struct.* V10 (2001) pp. 1115-1134.

Kiran, E. and Sen, Y.L. High-Pressure Viscosity and Density of n-Alkanes. *Int. J. Thermophys.* V13, No. 3 (1992) pp. 411-441.

Kirstein, Stefan et al. The influence of a viscous fluid on the vibration dynamics of scanning near-field optical microscopy fiber probes and atomic force microscopy cantilevers. *J. Appl. Phys.* V84, No. 4 (Aug. 15, 1998) pp. 1782-1790.

Klesewetter, L et al. Determination of Young's moduli of micromechanical thin films using the resonance method. *Sens. Actuators A*, V35 (1992) pp. 153-159.

Leissa, Arthur W. Vibration of plates, *NASA Special publication 160*, (1969).

Li, K.K. et al. Instrument for the remote determination of viscosity and density in hostile environments. *Rev Sci Instrum.*, V63 No. 9 (Sep. 1992) pp. 4192-4195.

Lindholm, Ulric S. et al. Elastic vibrations characteristics of cantilever plates in water. *J. Ship Res*. V9, (Jun. 1965) pp. 11-36.

Martin, Bret A. et al. Viscosity and Density Sensing with Ultrasonic Plate Waves. *Sens. Actuators* A21-A23, (1990) pp. 704-708.

Martin, S.J.; et al. Flexural plate wave resonator excited with Lorentz forces. *J. Appl. Phys.* V83, No. 9 (May 1, 1998) pp. 4589-4601.

Medani, M.S. and Hasan, M.A. Viscosity of Organic Liquids at Elevated Temperatures and the Corresponding Vapour Pressures *Can. J. of Chem. Eng.* V55 (Apr. 1977) pp. 203-209.

Mehl, James B. Analysis of Resonance Standing-Wave Measurements. *J. Acoust. Soc. Am.*, V64, No. 5 (Nov. 1978) pp. 1523-1525.

Moulin, A.M et al. Microcantilever-based biosensors. *Ultramicroscopy*, V82 (2000) pp. 23-31.

Nikanorov, S. P. Elastic Properties of Silicon. *Sov. Phys. Solid State* V13, No. 10 (Apr. 1972) pp. 2516-2518.

Oden, P.I. et al. Viscous drag measurements utilizing microfabricated cantilevers. *Appl. Phys. Lett.* V68, No. 26, (Jun. 24, 1996) pp. 3814-3816. 82.

Patois, et al. Measurement of fluid properties with a near-field acoustic sensor. *Appl. Phys. Lett.* V75, No. 2 (Jul. 12, 1999) pp. 295-297.

Patois, R. et al. Near-field acoustic densimeter and viscosimeter. *Rev Sci. Instrum.* V71, No. 10 (Oct. 2000) pp. 3860-3863.

Raiteri, R. et al. Micromechanical cantilever-based biosensors. *Sens. Actuators B*, V79 (2001) pp. 115-126.

Sadar, J. E. Frequency response of cantilever beams immersed in viscous fluids with applications to the atomic force microscope. *J. Appl. Phys.* V84, No. 1 (Jul. 1, 1998) pp. 64-76.

Sader, J.E. Surface stress induced deflections of cantilever plates with applications to the atomic force microscope: Rectangular plates *J. Appl.. Phys.* V89, No. 5 (Mar. 1, 2001) pp. 2911-2921.

Scaife, W.G.S. and Lyons, C.G.R. Dielectric Permittivity and pvT Data of Some n-alkanes. *Proc. R. Soc. London, Ser. A*, 370 (1980) pp. 193-211.

Shieh, J. et al. The selection of sensors. *Prog. Mat. Sci.* vol. 46, (2001) pp. 461-504.

Su, Y. Micromachined silicon cantilever paddles with piezoresistive readout for flow sensing. *J. Micromech. Microeng.* V6 (1996) pp. 69-72.

Tanaka, Y. Viscosity and Density of Binary Mixtures of Cyclohexane with n-Octane, n-Doecane, and n-Hexadecane Under High Pressures. *Int. J. Thermophys.* V12, No. 2 (1991) pp. 245-264.

Taylor, Sir Geoffrey. Analysis of the Swimming of Microscopic Organisms. *Proc. Roy. Soc. Ser. A*, V209 (Jun. 25, 1951) pp. 447-461.

Thundat, T. Detection of mercury vapor using resonating microcantilevers. *Appl. Phys. Let.*, V66, No. 13 (Mar. 27, 1995) pp. 1695-1697.

Van Dyke, Milton. Perturbation Methods in Fluid Mechanics, *Academic Press*: London, U.K. (1964) pp. 87-90.

Walters, D. et al. Short cantilevers for atomic force microscopy. *Rev. Sci. Instrum.* V67, No. 10 (Oct. 1996) pp. 3583-3590.

Weigert, Stefan et al. Frequency shifts of cantilevers vibrating in various media. *Appl. Phys. Lett.* V69, No. 19 (Nov. 4, 1996) pp. 2834-2836.

Werner, Matthias R. and Fahrner, Wolfgang R. Review on Materials, Microsensors, Systems, and Devices for High-Temperature and Harsh-Environment Applications. *IEEE Trans. Ind. Elec.* V48, No. 2 (Apr. 2001) pp. 249-257.

Woodward, J.G. A vibrating plates viscometer. *J. Acoust. Soc. Am.* V25, No. 1 (Jan. 1953) pp. 147-151.

Zhang, Yafan et al. A micromachined coriolis-force-based mass flowmeter for direct mass flow and fluid density measurement. *Transducers '01 Eurosensors XV, Proceedings of the 11th International Conference on Solid-State Sensors and Actuators, Munich, Germany* (Jun. 10 to 14, 2001) pp. 14601463.

* cited by examiner

FLUID PROPERTY SENSORS

This patent application claims priority from U.S. Provisional Patent Application No. 60/278,302, filed on Mar. 23, 2001, and U.S. Provisional Patent Application No. 60/286,293, filed on Apr. 26, 2001, both of which are incorporated herein by reference.

FIELD OF THE INVENTION

This invention relates to fluid property sensors and, more particularly, to sensors that are capable of measuring thermophysical (thermodynamic and transport) properties of fluids, such as oilfield fluids, under difficult conditions, such as downhole.

BACKGROUND

In the oil exploration and production industries, it is important to know the density and viscosity of reservoir fluids, such as crude oil or brine, at the pressure and temperature of the reservoir. These properties are used to determine the permeability and flow characteristics of the reservoir as well as the commercial value of the fluid in place. It is current practice to obtain a fluid sample downhole during the exploration phase of oilfield development and to determine the fluid's thermophysical properties at the surface. Although the pressure and temperature of the fluid sample at the surface can be adjusted to those at reservoir conditions, there is considerable difficulty in obtaining a sample that closely resembles the downhole fluid chemical composition owing to the volatility of lighter hydrocarbons, solids deposition, and drilling fluid contamination. The cost of retrieving a downhole sample and the difficulty of handling samples at the surface under downhole pressure and temperature conditions are both very high. Making measurements downhole will accelerate the evaluation process and reduce total costs. Decisions concerning reservoir production and optimization activities are often based on analyses of extremely small fluid samples obtained downhole, by volume relatively less than $10^{-9}$ of the reserves within a typical reservoir. The composition of a reservoir fluid can and will change during the lifetime of a reserve and thus the fluid properties will change. More frequent fluid property measurements, taken throughout the exploration and production process, would be extremely useful.

Downhole conditions are far more extreme than typical fluid property sensors are capable of operating under. At this time, fluids in a majority of producing hydrocarbon reservoirs are at downhole temperatures between (50 and 175) degrees Celsius, at downhole pressures between (100 and 2,000) bar, have densities in the range (500 to 1300) kg m$^{-3}$, and have viscosities on the order of (1 to 1000) mPa s. Oilfield equipment typically must pass rigorous shock and corrosion resistance standards, due to the difficult deployment environment and the possible presence of corrosive fluid constituents such as $H_2S$ and $CO_2$. Reservoir fluids are often extremely complex and may contain chemical components ranging from asphaltenes and waxes to methane. In this environment, it is necessary to have a fluid sensor that can operate accurately in this complicated and harsh environment. No commercially available device exists today that would satisfy these requirements. Fluid property sensors are also utilized in many other industries, such as the water industry, the chemical processing industry, and the food processing industry. Improved fluid property sensors could offer substantial benefits to these types of industries as well.

SUMMARY OF INVENTION

The present invention includes a range of devices, based on Micro-Electro Mechanical Systems (MEMS) technology, for analyzing or measuring thermophysical properties (such as density and viscosity) of fluids (such as oilfield reservoir fluids) under difficult conditions, such as downhole. The fluid property sensors of this invention may be embedded in a well completion or in the formation; alternatively, these devices may be incorporated into downhole sampling tools, such as the Schlumberger Modular Formation Dynamics Tester (MDT), or in sample bottles designed to hold reservoir fluid samples under downhole conditions.

In accordance with the invention, a MEMS based fluid sensor includes a planar member machined from a substrate material, an electrical conductor formed at least partly on the planar member, and a gauge formed on the planar member. The gauge is adapted to measure a physical effect on the planar member that is indicative of a property of a fluid in contact with the planar member.

In a preferred embodiment, the sensor includes: a monolithic structure, machined from a substrate material, having a support portion allowing the monolithic structure to be attached to another structure, a plate portion capable of oscillating, and a flexible beam portion that decouples stress in the support portion from motion induced stress in the plate; means for producing a magnetic field; an electrical conductor, formed at least partly on the plate, allowing current flowing through the electrical conductor to interact with the magnetic field to induce oscillation of the plate; a strain sensor, formed on the monolithic structure, adapted to detect movement of the plate; and means for determining a thermodynamic property of a fluid in contact with the plate using the strain sensor detected plate movements.

Further details and features of the invention will become more readily apparent from the detailed description that follows.

BRIEF DESCRIPTION OF FIGURES

The invention will be described in more detail below in conjunction with the following Figures, in which.

DETAILED DESCRIPTION

The present invention describes a range of electromechanical sensors that have been adapted for analyzing and measuring thermo-physical properties of oilfield fluids under downhole conditions. The electromechanical sensors of this invention are micro-machined out of a substrate material and are fabricated using technologies that have been developed to produce electronic integrated circuit (IC) devices at low cost and in large quantities (batch fabrication). Devices of this type are typically referred to as Micro-Electro-Mechanical Systems (MEMS) devices, and the inventors believe the present invention describes the first application of MEMS technology to downhole oilfield fluid property sensing.

The MEMS based sensors of the present invention include a planar member machined from a substrate material, an electrical conductor formed at least partly on the planar member, and some sort of gauge formed on the planar member. When the planar member is put into contact with a fluid, such as an oilfield fluid, and the MEMS based sensor is activated, the gauge measures a physical effect on the planar member that is indicative of an oilfield fluid property.

Figure 1:
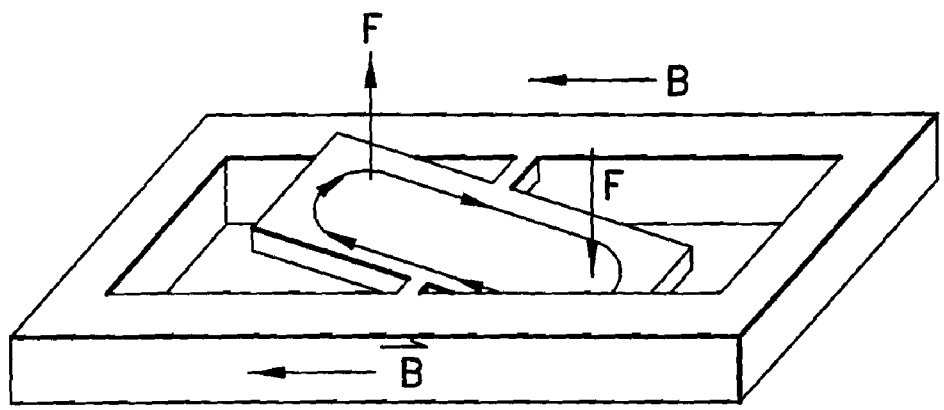
FIG. 1 schematically illustrates a magnetic field B interacting with a current i flowing atop a planar member to generate a force F on the member in accordance with certain embodiments of the invention.

In some embodiments of the invention, the planar member includes a movable element that is attached to the planar member, and the electrical conductor forms a conducting coil on the planar member through which electrical current ($\bar{I}$) flows when the sensor is activated. In the presence of a magnetic field ($\bar{B}$) applied approximately parallel to the surface of the planar member, the flowing current interacts with the magnetic field to produce Amperian forces ($\bar{F}$) (also referred to as Laplace or Lorentz forces) on the movable element, as illustrated in FIG. 1. The forces act on the movable element at a frequency determined by the applied current ($\bar{I}$) and set it vibrating or oscillating. The gauge in these embodiments senses the movement of the oscillating element using a strain sensor, such as a Wheatstone bridge of piezoresistors, a back-EMF sensor, or an electrical impedance sensor. It is often advantageous to include gauges at different positions on the planar member to distinguish between different modes of oscillation. Each mode of oscillation has a characteristic resonant frequency ($f^{vac}$) at which the amplitude of oscillation (S) is a maximum. When these sensor embodiments are contacted with a fluid, the oscillating element causes the fluid around it to move, adding effective mass, or inertia, to the element's intrinsic mass and causing a decrease in the resonant frequency ($f<f^{vac}$). Fluid shear around the element leads to viscous energy dissipation and causes the quality factor of the oscillator ($Q^{vac}$) to decrease as well ($Q<Q^{vac}$) Calibration of these sensor embodiments typically involves identifying different modes of oscillation, their resonant frequencies, and the quality factor of the oscillator.

These sensor embodiments relate measurements of the resonant frequency, $f_0$, and quality factor, Q, to the density and viscosity of the fluid. For typical oilfield fluids, which have a density ($\rho$) in the range (500 to 1300) kg m$^{-3}$ and viscosity ($\eta$) on the order of (1 to 1000) mPa s, the quality factor may be expressed as:

$$Q = ak\sqrt{\frac{\omega_0}{\eta\rho}}. \qquad (1)$$

where a is a term describing the effective mass or inertia of the oscillating element and k is a constant related to the geometry of the oscillating element. The resonant circular frequency ($\omega_0 = 2\pi f_0$) of the oscillating element may be generally expressed as $$\omega_0 = \sqrt{c/a} \qquad (2)$$

where c is a term describing the elastic restoring force or torque which acts on the element's mass to return it to its initial position following a perturbation, such as $\bar{F}$ acting on the element. Solving equation (2) for a and substituting in equation (1) gives $$Q = \frac{ck}{\omega_0^{3/2}\sqrt{\eta\rho}}. \qquad (3)$$

The constants c and k typically depend only on the geometry and composition of the oscillating element, and so may be determined by calibrating the sensor using fluids of known density and viscosity. Moreover, assuming the Reynolds number is much greater than one, which is generally a sound assumption with these sensor embodiments and typical oilfield fluids, then the mass that the fluid movement effectively adds to the oscillating element is proportional only to the fluid density. Thus, from equation (2) it follows that:

$$\frac{\omega_0^{vac}}{\omega_0} \approx (1 + k\rho)^{1/2}. \qquad (4)$$

Thus, fluid density ($\rho$) may be obtained using equation (4) by measuring $\omega_0^{vac}$ and $\omega_0$, and, once $\rho$ is known, fluid viscosity ($\eta$) may be obtained from equation (3) by additionally measuring Q.

The density and viscosity may also be determined using the following formulas:

$$\rho(B, T, p) = \frac{4A_1}{\pi Y} \cdot \left\{ \frac{W\rho(Si, T, p)}{\{f(B, T, p)/f(p=0)\}^2} - W\rho(Si, T, p) - \left[\frac{A_2\sqrt{\eta(B, T, p)\rho(B, T, p)}}{\sqrt{\pi f(B, T, p)}}\right] \right\}. \qquad (5)$$

and $$\eta(B, T, p) = \left[\frac{A_3}{Q(2\pi f(B, T, p))^{3/2}}\right]^2 \bigg/ \rho(B, T, p). \quad (6)$$

where $A_1$, $A_2$, and $A_3$ are adjustable parameters that are determined by calibrating the sensor with known fluids, $\rho(B,T,p)$ is the density of the fluid being sensed (B) at temperature T and pressure p, Y is the width of the oscillating element, W is the thickness of the oscillating element, $\rho(Si,T,p)$ is the density of silicon (the material the oscillating element comprises) at temperature T and pressure p, f(B,T,p) is the resonant frequency of the sensor when immersed in the fluid being sensed at temperature T and pressure p, f(p=0) is the resonant frequency of the sensor in a vacuum, $\eta(B,T,p)$ is the viscosity of the fluid being sensed (B) at temperature T and pressure p, and Q is the resonance quality factor that is described above.

Figure 2:
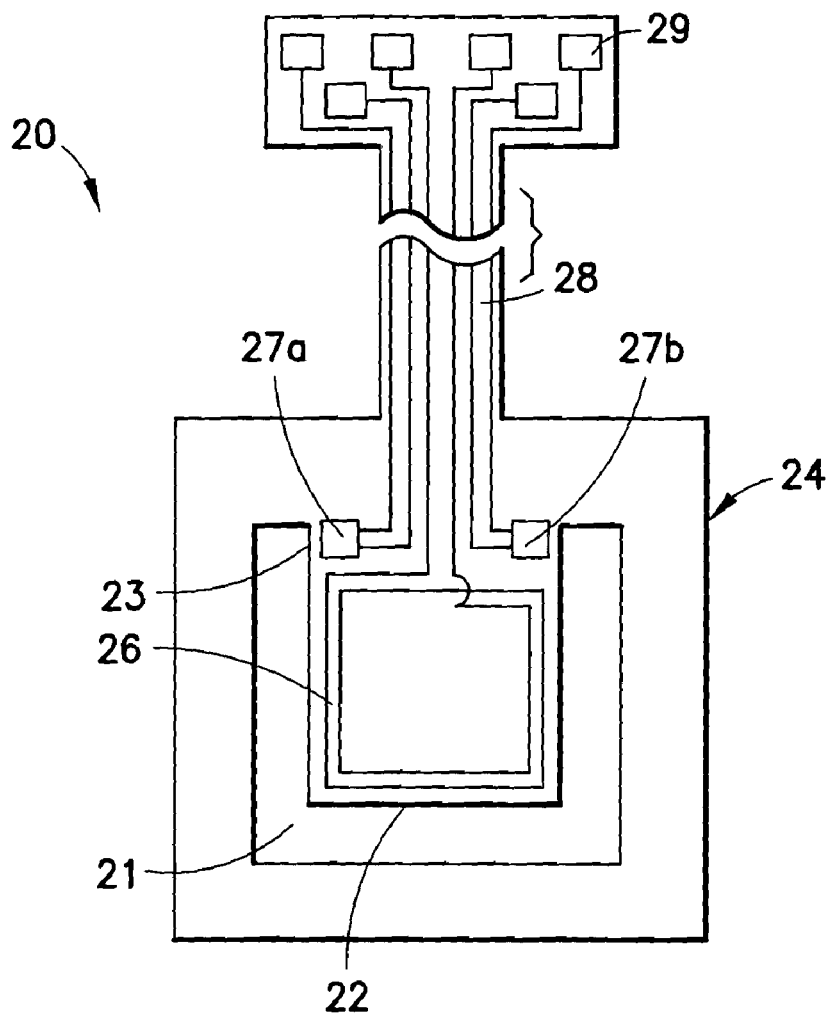
FIG. 2 schematically illustrates one embodiment of a MEMS-fluid sensor according to the invention.
Figure 3:
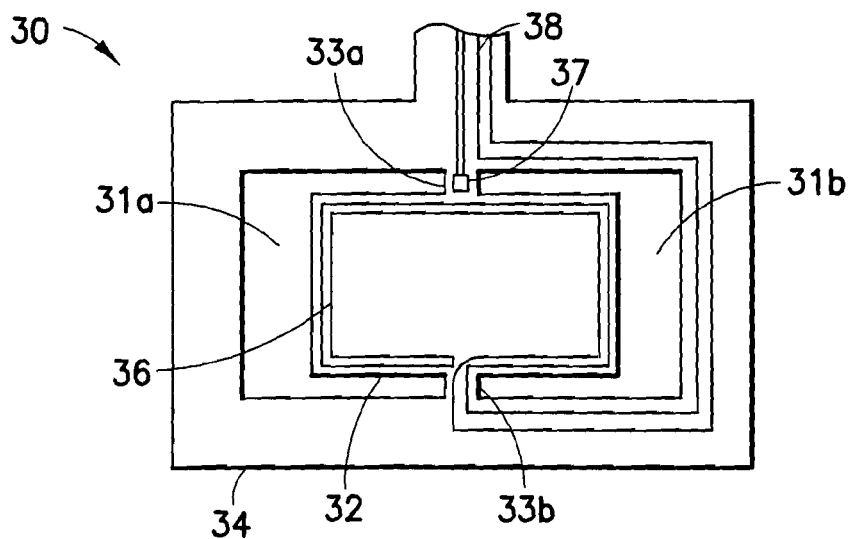
FIG. 3 schematically illustrates a second embodiment of a MEMS-fluid sensor according to the invention.
Figure 4:
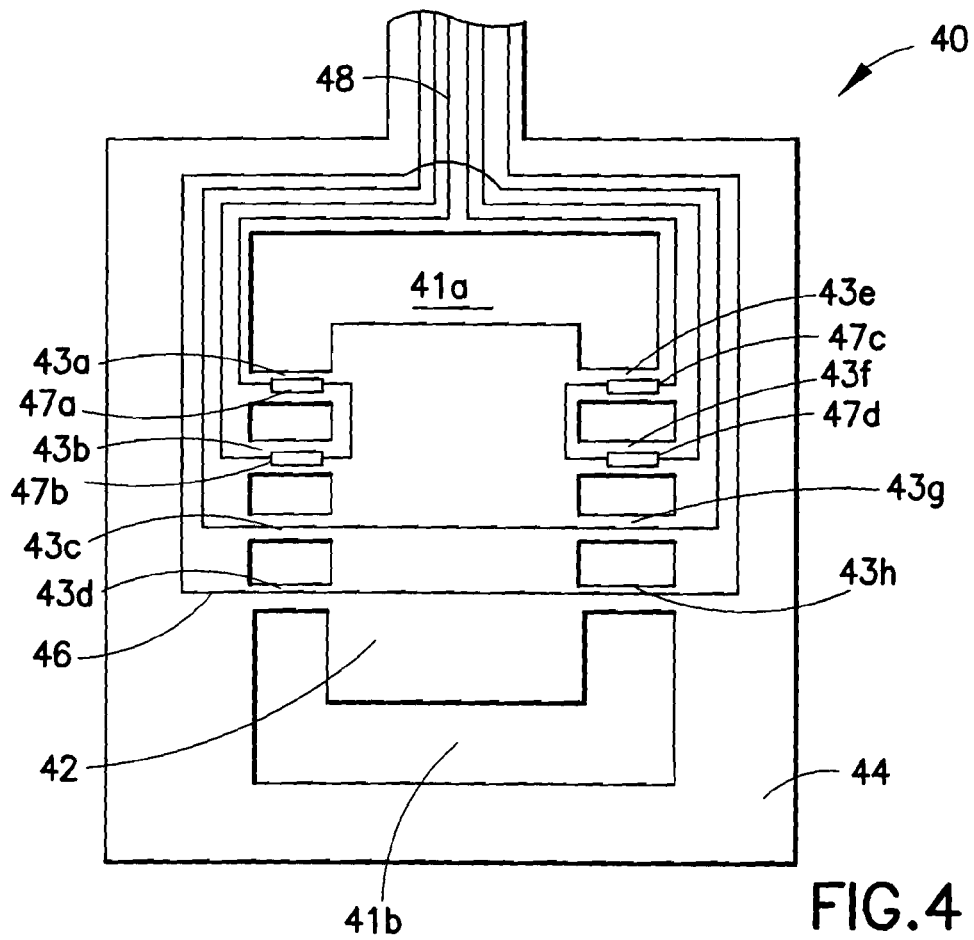
FIG. 4 schematically illustrates a third embodiment of a MEMS-fluid sensor according to the invention.

FIGS. 2-4 illustrate sensor embodiments that operate according to these principles. FIG. 2 schematically illustrates a flexural plate embodiment of a MEMS based sensor 20 that has a monolithic structure, planar member 24, machined from a semiconductor substrate. A portion, flexural plate 22, is thinned and cut (or etched) from the (thicker) planar member 24, and remains attached to the planar member along one side 23. An electrical conductor extends from the planar member to form a conducting coil 26 atop the plate 22. In this particular embodiment, two strain gauges 27a, 27b are shown near the corners of the side at which the plate 22 attaches to the planar member 24, where maximum strain occurs during the oscillatory movement of the plate. Computer modeling may be used to determine where the maximum strain will occur. Two strain gauges are used to allow the oscillation mode to be identified. Electrical connectors 28 are shown extending to connection pads 29 on a support portion of the structure that may be used to wire bond the sensor to a printed circuit board or otherwise connect the sensor with various electrical devices that would be used to activate and interrogate the various sensor elements. Connection pads 29 are formed on a support portion of the planar member 24 that allows the sensor 20 to be mounted or attached to another structure. Between the support portion and the plate portion of the planar member 24 is a flexible beam portion that decouples stress in the support portion from motion induced stress in the plate.

A fluid in contact with this sensor embodiment would surround the flexural plate 24 and fill the area 21 so that, when activated, the flexural plate would vibrate and cause the fluid to move and effect the resonant frequency and quality factor of the plate, as described above. Although the designs shown in FIG. 2 and in subsequent Figures have predominantly rectangular features, may leave a portion of the planar member 26 surrounding the plate 22, or may produce a section of the planar member 26 between the plate 22 and the connection pads 29 that is narrower in width than the plate 22, it should be recognized that these features (as well as certain other common features) represent optional, not required, features of the inventive sensors.

FIG. 3 shows a torsional plate embodiment of a MEMS based sensor 30. A torsional plate 32 is etched or cut from a planar member 34 and remains attached to the planar member by two arms 33a-b extending from opposite sides of the plate. An electrical conductor extends from the planar member 34 and across one of the arms 33b to form a conducting coil 36 atop the plate 32. A strain gauge 37 is partially formed on at least one of the arms 33a, where the maximum strain occurs during the oscillatory movement of the plate. Electrical connectors 38 may extend to connection pads (not shown) used to wire bond the sensor to a printed circuit board, or otherwise lead to connections between the sensor and various electrical devices that would be used to activate and interrogate the various sensor elements. A fluid in contact with this sensor embodiment would surround the plate 32 and fill the areas 31a-b so that, when activated, the torsional plate would oscillate and cause the fluid to move and effect the resonant frequency and quality factor of the plate, as described above.

FIG. 4 shows still another embodiment of a MEMS based sensor 40. This device could be used to measure viscosity. A movable plate 42 is cut or etched from a planar member 44 and remains attached to the planar member by a plurality of arms 43a-h extending from opposite sides of the plate. An electrical conductor extends from the planar member across some of the arms 43c-d and 43g-h to form a conducting coil 46 partially atop the plate 42. A plurality of strain gauge resistors 47a-d in the form of a Wheatstone bridge is formed on some of the arms 43a-d. Electrical connectors 48 may extend to connection pads (not shown) used to wire bond the sensor to a printed circuit board, or otherwise lead to connections between the sensor and various electrical devices that would be used to activate and interrogate the various sensor elements. A fluid in contact with this sensor embodiment would surround the plate 42 and fill the areas 41a-b so that, when activated, the movable plate would vibrate and cause the fluid to move and change the resonant frequency and quality factor of the plate, as described above. In this embodiment, a magnetic field is applied perpendicular to the plate 42 to induce shear mode oscillation of the plate.

Figure 5:
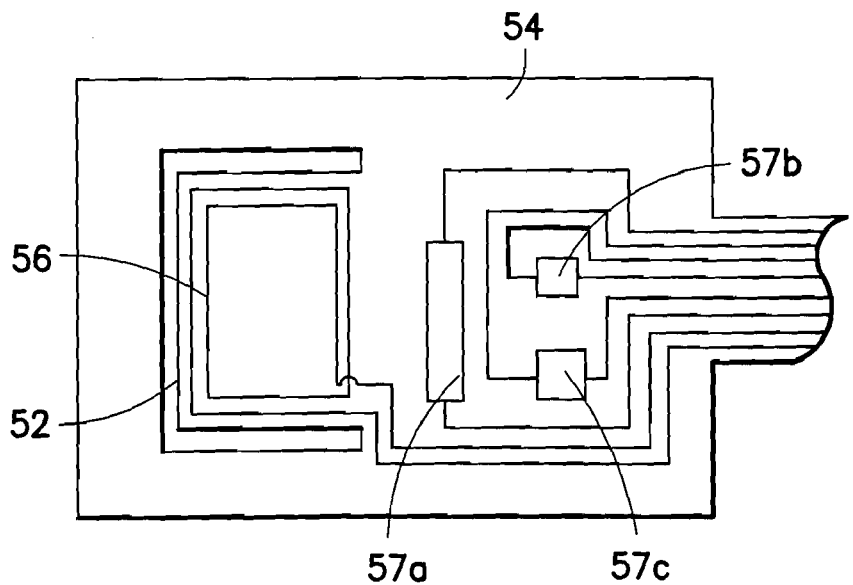
FIG. 5 schematically illustrates a fourth embodiment of a MEMS-fluid sensor according to the invention.

The embodiments shown in FIGS. 2 to 4 take advantage of the Amperian forces generated by the interaction of a current flowing in a conducting coil and a magnetic field to activate a moveable element and consequently measure the density and/or viscosity of a fluid. FIG. 5 shows one embodiment of a MEMS based sensor that takes advantage of the Amperian forces acting on a moving element to acoustically induce and detect the onset of bubble formation. Knowledge of the bubble point is important in oil production because if the borehole pressure drops below the bubble point pressure, gas bubbles can form in the reservoir, leading to a decrease in the oil phase relative permeability. A movable element, shown in FIG. 5 as a flexural plate 52, is etched or cut from a planar member 54. An electrical conductor forms a conducting coil 56 atop the element 52. In the presence of a magnetic field, a current flowing through the conducting coil creates forces on the element that cause the element to vibrate and to act as an acoustic transducer. The acoustic waves generated by the vibrating element can, in a process known as cavitation, lead to bubble evolution in a fluid at or near its bubble point pressure and temperature. To sense the presence of bubbles, the gauge of this embodiment may include a differential pressure gauge 57a, as well as a thermometer 57b and an absolute pressure gauge 57c, as shown in FIG. 5. Alternatively, changes in electrical properties of the acoustic transducer may be used to detect bubble formation, as described in U.S. Pat. No. 6,128,949.

Figure 6:
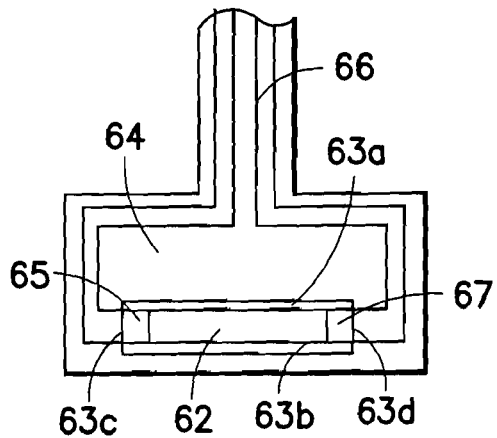
FIG. 6 schematically illustrates a fifth embodiment of a MEMS-fluid sensor according to the invention.

The present invention also encompasses MEMS based sensors that do not include a movable element nor rely on Amperian forces to work. For example, FIG. 6 shows one embodiment of a MEMS based hot wire anemometer, which may be used to measure the thermal conductivity of a reservoir fluid. An elongated element 62 is etched or cut from a planar member 64 along two opposing sides 63a-b, so that the elongated element remains attached to the planar member along its ends 63c-d. A heater 65, such as a resistance heater, is formed atop the element 62 near one of the ends 63c, and a heat gauge 67, such as a resistance thermometer, is formed near the opposite end 63d of the elongated element from the heating element. Electrical conductors 66 couple the heater 65 and the heat gauge 67 with various electrical devices (not shown) that would be used to operate them. When in contact with a reservoir fluid and activated, the heater heats the fluid surrounding it around one end of the elongated element, and the heat gauge monitors the change in temperature as the fluid conveys the heat outwardly, including towards the opposite end of the elongated element. The time-rate of change in temperature monitored by the heat gauge may be calibrated to the fluid's thermal conductivity and viscosity.

Figure 7:
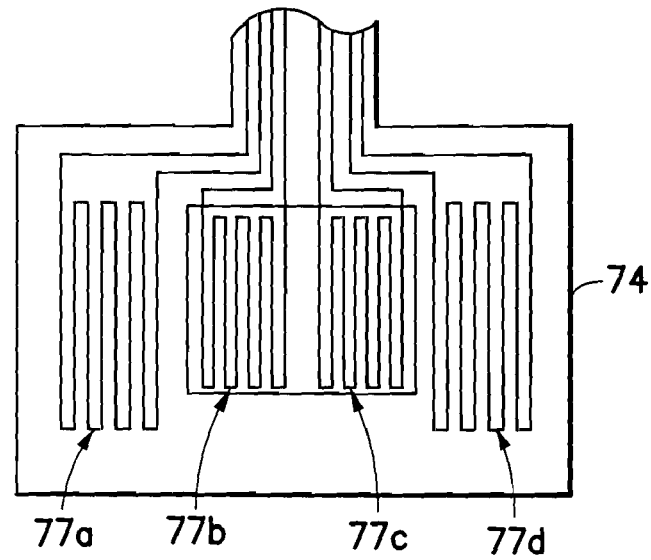
FIG. 7 schematically illustrates a sixth embodiment of a MEMS-fluid sensor according to the invention.

Another example of a MEMS based sensor encompassed by the present invention is shown in FIG. 7. FIG. 7 shows one embodiment of a MEMS based hot wire flow calorimeter, which may be used to determine the heat capacity/thermal conductivity and phase transition temperatures of a reservoir fluid. Four heating resistors 77a-d are formed in a Wheatstone bridge atop a planar member 74. The center of the planar member where the two central resistors 77b, c are placed is etched or cut away so that fluid may flow around and between the two central resistors ensuring good thermal contact with them. The outer two resistors 77a, d do not have the same degree of thermal contact with the fluid due to the protection provided by the relatively thick planar member. When activated, the central resistors will reach a temperature different from that of the outer resistors, the difference of which depends on the heat capacity of the surrounding fluid. Due to the excellent temperature sensitivity of silicon, the temperature difference will induce an early measurable voltage imbalance in the bridge.

The heat generated by the central resistors may also be used to induce a phase transition in the surrounding fluid and so monitor the phase transition temperature. The dielectric constant of a reservoir fluid may be measured using a MEMS based sensor similar to that described above, with capacitors replacing the resistors shown in FIG. 7.

Various MEMS based sensors of the types described above may be fabricated onto a single monolithic substrate or may be physically packaged together and used to measure sufficient properties to determine equation of state parameters that can then be used to calculate the physical properties of the reservoir fluids under virtually any conditions likely to be found in the reservoir fluid production stream. A different minimum set of sensor types may be desired for each major type of fluid regime. This type of integrated sensor packaging and joint fluid property inversion is particularly helpful with respect to downhole hydrocarbon samples because adjacent sensors would be making measurements on virtually identical fluid samples and can be expected to deliver a self-consistent set of data values. Getting self-consistent data is often problematic when hydrocarbon samples being kept at downhole pressure and temperature conditions are analyzed at the surface because a series of different analysis equipment is often used and it is difficult or impossible to ensure that the fluid samples seen by each of these pieces of equipment is virtually identical.

The sensors of the present invention may be micro-machined out of a wafer substrate. Silicon, such as poly-silicon and in particular mono-crystalline silicon, with its good elastic properties and small internal vibration losses, is the presently preferred material for many embodiments of the present invention. Most integrated circuit (IC) technology has been developed for silicon processing, which is an additional advantage for the present invention. Other materials, such as silicon carbide, however, possess properties, in particular chemical stability, that may be advantageous for oilfield fluid property sensors in general, and IC-processing techniques for these materials are also known. Thus, it is to be understood that the sensors of the present invention may be made out of a variety of materials.

Embodiments of the present invention, such as those described above with reference to FIGS. 2 to 7, have been processed from a silicon on insulator (SOI) wafer with a 350 µm thick silicon substrate layer and a 20 µm thick layer of mono-crystalline silicon separated by a 0.5 µm thick silicon oxide layer. The exposed surface of the 20 µm thick layer of mono-crystalline silicon was oxidized to a depth of about 0.3 nm and atop this a 400 nm thick layer of polysilicon was deposited. The whole assembly was annealed. The polysilicon layer was then doped with boron, coated with an UV sensitive photoresist and exposed to ultraviolet radiation in the presence of a mask. The exposed polysilicon was removed in a reactive ion etching step to the 0.3 nm silicon oxide layer formed at the surface of the 20 µm thick mono-crystalline silicon layer to form piezoresistors, which are the active element of a Wheatstone bridge strain gauge. Silicon nitride ($Si_xN_y$) was deposited atop the surface coated in etched poly-silicon, with a chemical vapor deposition step to form a chemically inert and insulating layer. The resulting layer underwent photolithography and etching steps to allow electrical contact to be made to the underlying poly-silicon layer. A layer of aluminum was deposited to form the electrical contacts, and underwent photolithography and etching steps to leave a connection to the piezoresistors for wire-bonding, to form the conducting coil atop the movable element, and to provide the connection between the coil and the connection pads. A second layer of silicon nitride ($Si_xN_y$) was deposited atop the aluminum and etched poly-silicon layers in a plasma-enhanced chemical vapor deposition step to form a chemically inert layer, which was then etched to provide an open area for wire bonding. The geometry of the movable element is defined by structuring the 20 µm silicon layer using photolithography and plasma etching. Other types of passivation layers may be used, such as silicon carbide, diamond-like carbon, and/or polytetrafluoroethylene materials. Finally, the 350 µm mono-crystalline silicon substrate below and around the defined geometry is removed with a back-etching process to relieve the movable element.

It is to be understood that while the inventors have chosen these particular parameters (materials, dimensions, doping levels, etc.) and have used these particular steps, other parameters and other processing steps may be used to manufacture sensors according to the present invention. Thus, the present invention is not intended to be limited to sensors manufactured according to the set of parameters or series of processing steps described herein.

Figure 8:
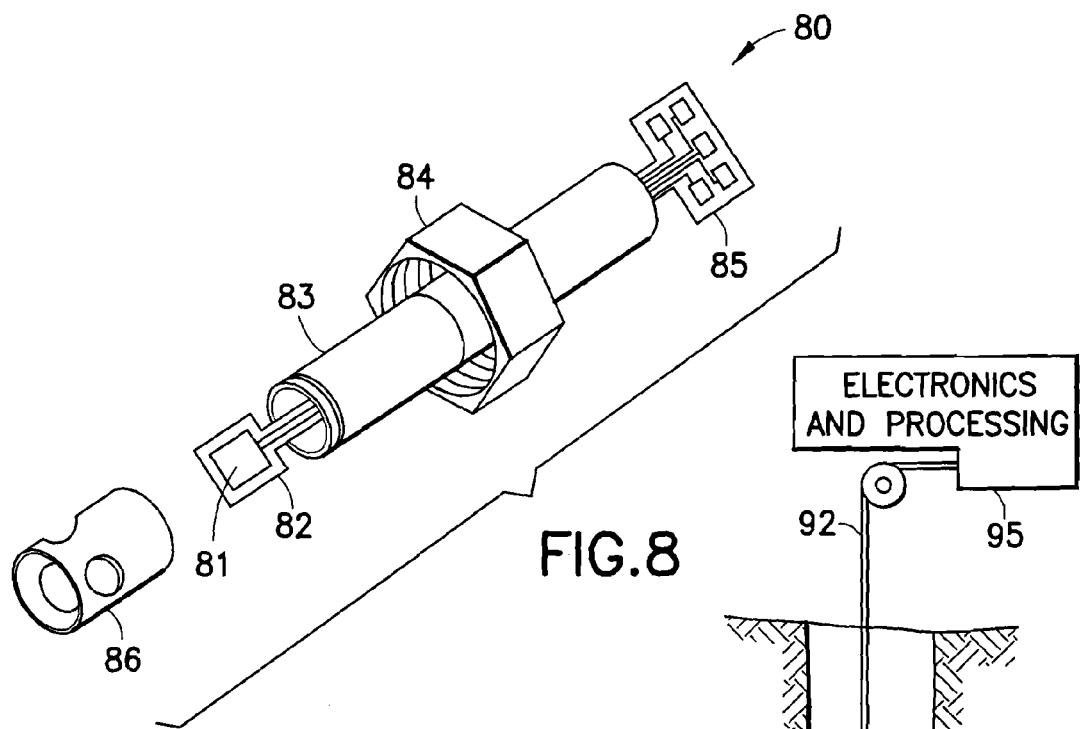
FIG. 8 shows one embodiment of a MEMS-fluid sensor and associated mounting hardware.

FIG. 8 shows one embodiment of a MEMS based sensor adapted to be introduced and fit to a pressure vessel, such as a reservoir fluid sample bottle of the kind commonly used to transport and store reservoir fluid samples under downhole conditions. An example of such a sample bottle may be found in commonly-owned published UK Patent Application No. GB 2,348,222 A. The MEMS based sensor device 81 is shown wire-bonded to a printed circuit board 82 that is fed-through and mounted in a tube 83. The tube 83 is fit with a compression or other type of fitting 84 capable of forming a pressure-tight seal when the assembly 80 is fit to a pressure vessel. When fit to a pressure vessel, connection pads 85 formed on the printed circuit board remain exposed to be coupled with the electrical equipment used to activate and monitor the MEMS based sensor. The embodiment of FIG. 8 is shown with a removable cap 86 that can be placed over the MEMS based device to provide a degree of protection from the environment while allowing fluid to contact the MEMS based device. In some embodiments, a permanent magnet (not shown) may be housed in the cap or deposited on the MEMS based device to provide a magnetic field required for actuation of the device. Alternatively, an electro-magnet may be housed in the cap, or formed on the MEMS based device, for the same purpose.

A MEMS based device according to the present invention of course may be packaged differently, the assembly being adapted to use already existing electrical feed-throughs and ports on a sample bottle. In addition to measuring properties of oilfield fluids being stored and/or transported in sample bottles, the MEMS based sensor devices may be adapted for use in downhole fluid sampling tools, such as Schlumberger's MDT tool, or in permanent reservoir monitoring applications.

Figure 9:
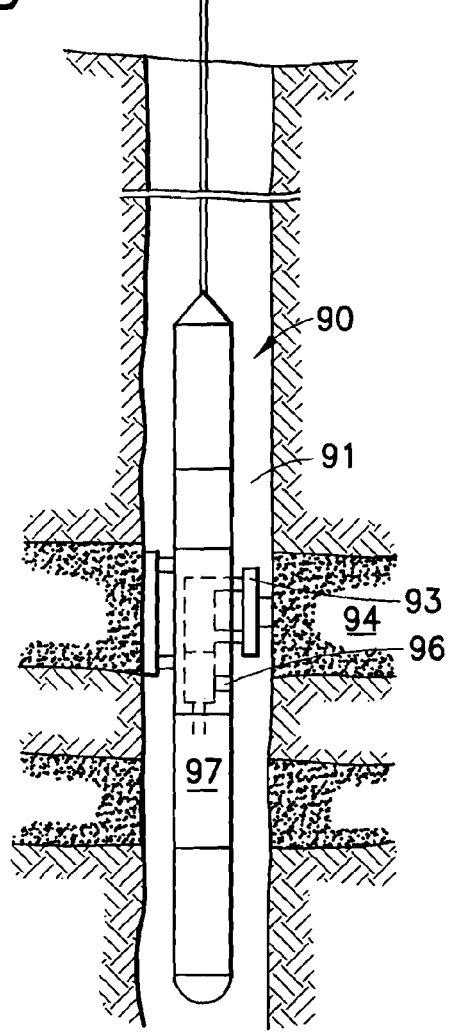
FIG. 9 schematically illustrates uses of MEMS-fluid sensors according to the invention in connection with certain hydrocarbon exploration and production activities.

FIG. 9 schematically illustrates certain uses of MEMS fluid sensors according to the invention in connection with hydrocarbon exploration and production activities. In FIG. 9, a fluid sampling tool 90 has been lowered within borehole 91 on a cable 92 until the probe portion 93 of the tool is adjacent to the desired formation 94. The electronics and processing unit 95 then instructs the fluid sampling tool 90 to withdraw a sample of the reservoir fluid from the desired formation 94. The withdrawn fluid sample may pass by a MEMS based sensor 96, where various fluid properties are determined, and/or may be stored within an intelligent sample bottle 97 that has an integrated MEMS based sensor that allows the fluid properties to be determined after the sample is returned to the surface.

Figure 10:
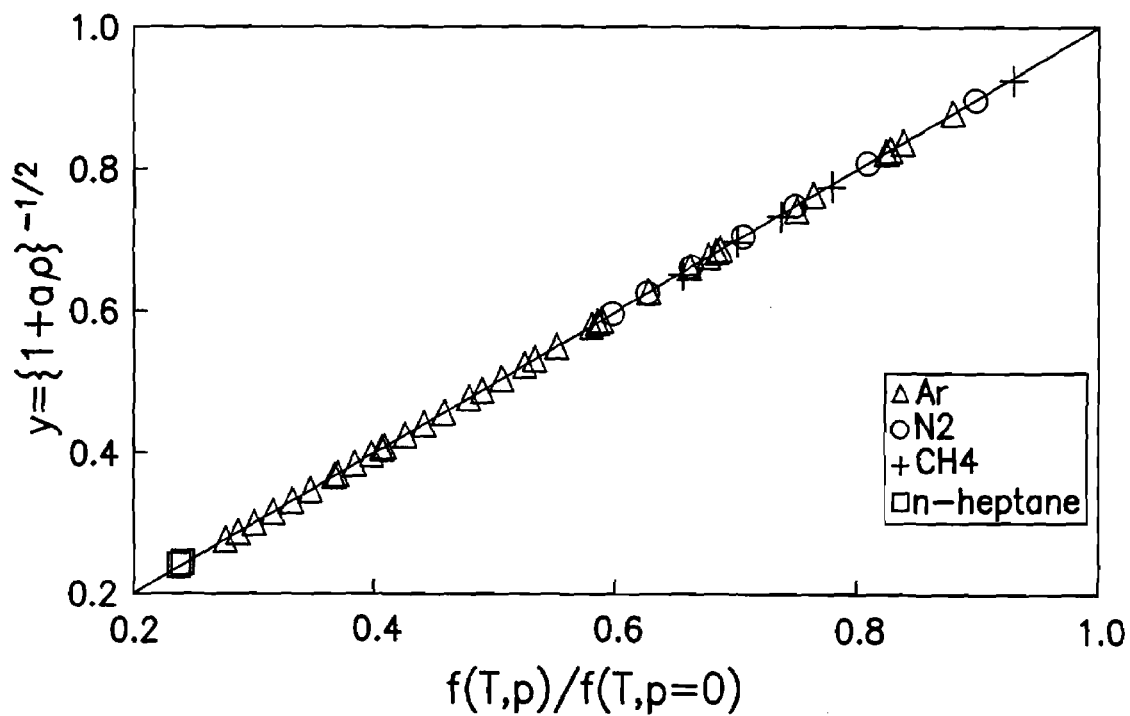
FIG. 10 shows values obtained from equation (4) plotted as a function of the resonance frequency, normalized to the resonance frequency in a vacuum (p=0), of a flexural plate embodiment of a MEMS-fluid sensor of the type shown in FIG. 2.
Figure 11:
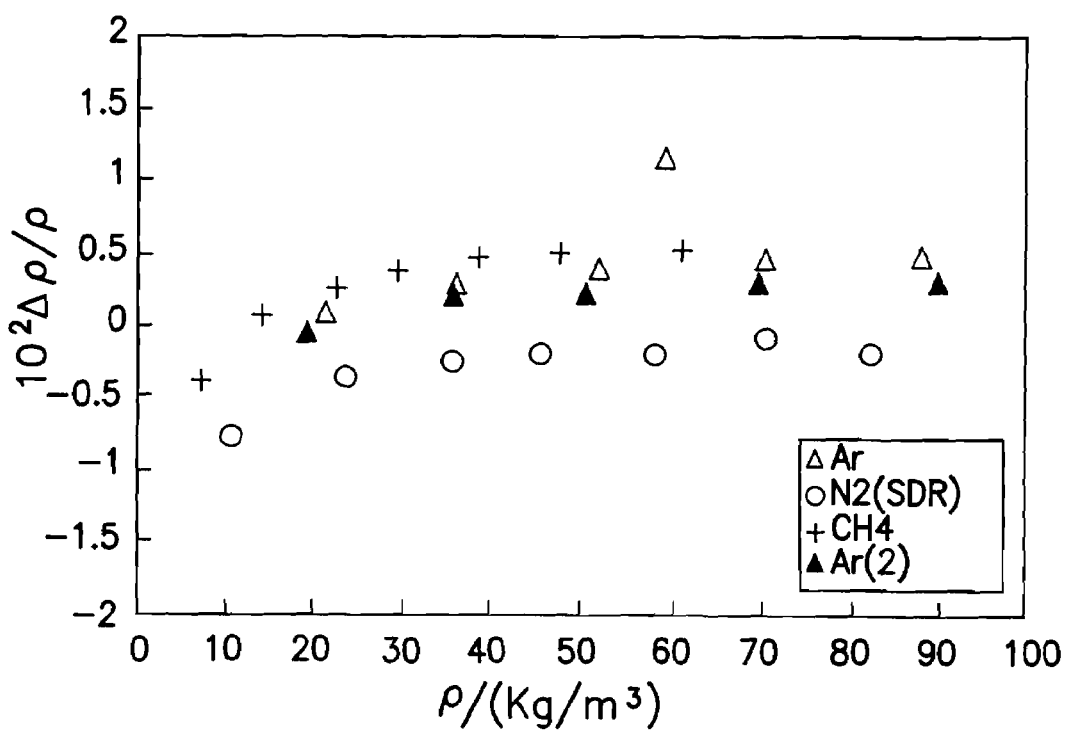
FIG. 11 shows fractional differences of density determined using a flexural plate embodiment of a MEMS-fluid sensor of the type shown in FIG. 2 and the true density calculated from an equation of state.
Figure 12:
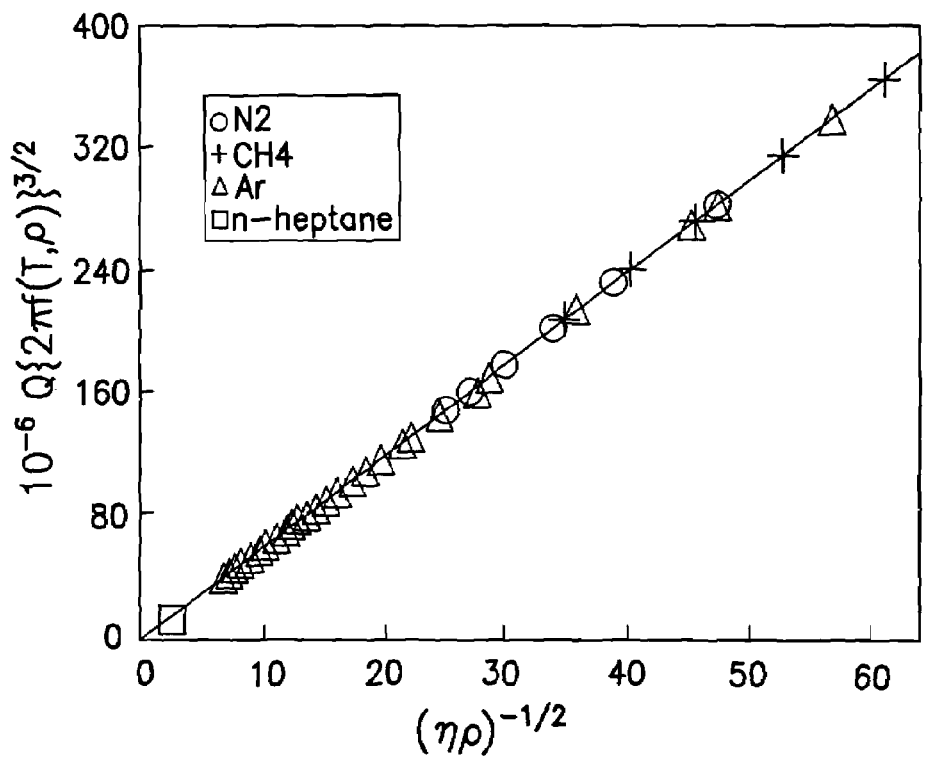
FIG. 12 plots quality factor as a function of $(\eta\rho)^{-1/2}$, where $\eta$ is the viscosity and $\rho$ is the density, of a flexural plate embodiment of a MEMS-fluid sensor of the type shown in FIG. 2.
Figure 13:
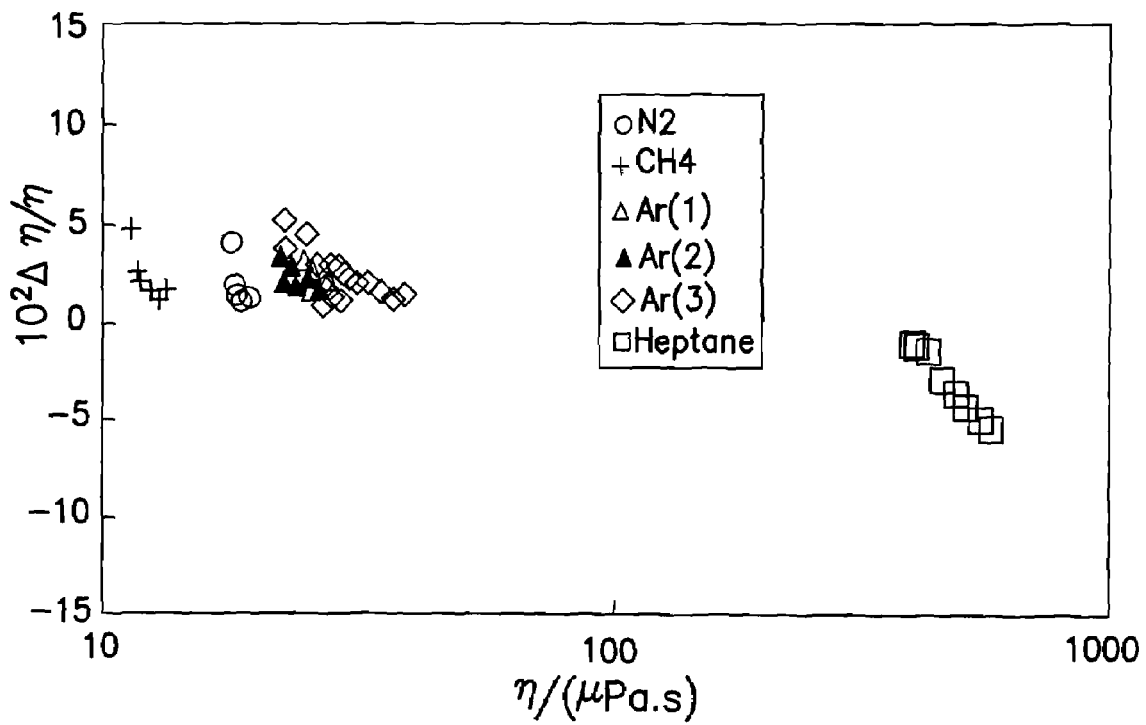
FIG. 13 shows relative difference in viscosity (determined by subtracting the true viscosity calculated from an equation of state from the viscosity determined using a flexural plate embodiment of a MEMS-fluid sensor of the type shown in FIG. 2 and then dividing the result by the true viscosity) as a function of viscosity $\eta$.
Figure 14:
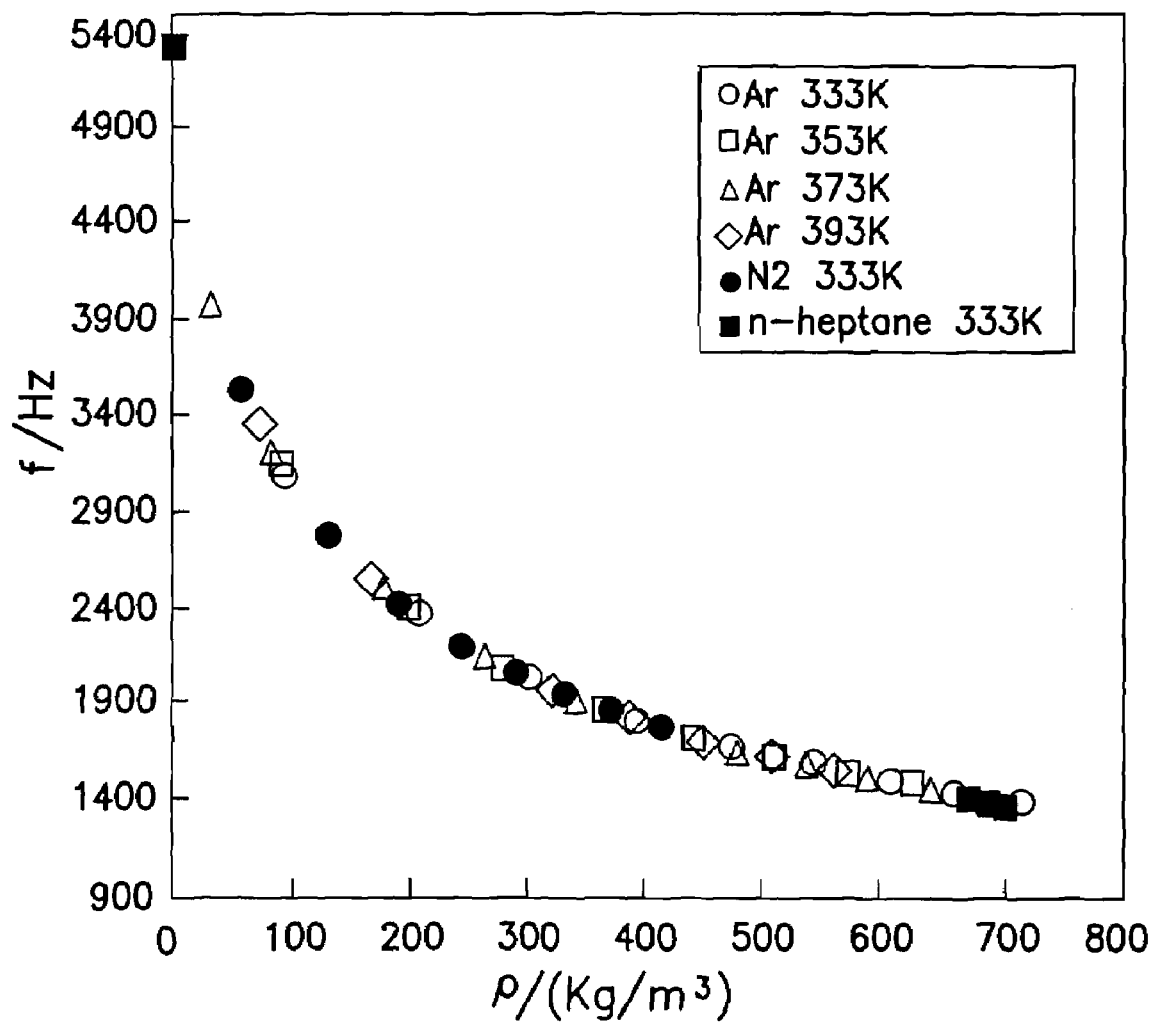
FIG. 14 shows the frequency f versus density $\rho$ response of a MEMS-fluid sensor of the type shown in FIG. 2 over a wide range of fluid densities.

A flexural plate MEMS based sensor embodiment, of the type shown in FIG. 2, was mounted as described above and tested in fluids with densities from approximately 1 kg/m$^3$ to 1900 kg/m$^3$ and viscosities from approximately 18 µPa·s to 2 Pa·s, where the resonance frequency ranged from about 5000 Hz to 500 Hz and the quality factor ranged from about 200 to 2. The complex resonance frequency was determined while the device was surrounded by argon, methane, and nitrogen at densities below 145 kg/m$^3$. The values obtained with argon were used to obtain the constant k in equation (4) above. The results are shown in FIG. 10, as a function of the frequency normalized to $f_0^{vac}$. The densities obtained from the resonance frequency using equation (4) are shown in FIG. 11 as fractional deviations from values obtained from the equations of state package known under the acronym NIST 14. The majority of the differences are less than 0.5%. Similar results were obtained at densities up to 1100 kg/m$^3$. Equation (3) shows the product of the resonance quality factor and the term $(\eta\rho)^{-1/2}$ is a constant; FIG. 12 confirms this expectation, where the solid line, which fits the imaginary component of the resonance for nitrogen, represents the results for all three gases. The relative deviation of the viscosity obtained with the calibration based solely on nitrogen from that obtained from NIST 14 is, as shown in FIG. 13, less than 10%. The frequency f versus density ρ response of a MEMS-fluid sensor of the type shown in FIG. 2 over an extremely wide range of fluid densities, from nearly zero to 700 mg/m$^3$, is shown in FIG. 14.

These types of sensors have the significant advantage that they do not have to be calibrated for each range of fluid types the sensor is expected to encounter and for each set of operating conditions the sensor will be used in. This wide spectrum of valid operating conditions is particularly important downhole because such a broad range of downhole fluids are commonly encountered. By having a very thin plate, the sensor is very sensitive to the fluid properties. For one moving plate embodiment of the present invention, the plate is approximately 2.8 millimeters wide, approximately 2.3 millimeters long, and approximately 20 micrometers thick, resulting in the weight of the moving plate being on the order of 0.30 milligrams. In comparison, the mass of water moved by the plate is estimated to be on the same order as the mass of the plate, and these roughly similar masses helps to account for the excellent sensitivity of the device. The primary oscillation mode resonance frequency for this embodiment in a vacuum is approximately 5.3 kHz. Highly decoupled excitation and detection systems greatly simplify the electronics and ensures a very accurate measurement down to the very low values of Q that may be encountered in very viscous fluids. MEMS based sensor embodiments of the type shown in FIG. 2 are typically quite insensitive to temperature changes as well. Silicon construction aids in long term stability, as well, because silicon does not creep like many other materials.

The invention has been described herein with reference to certain examples and embodiments. It will, however, be evident that various modifications and changes may be made to the embodiments described above without departing from the scope of the invention as set forth in the claims.

We claim:

1. A Micro-Electro Mechanical Systems (MEMS) based reservoir fluid sensor adapted for downhole conditions comprising:
   a) a planar member machined from a substrate material;
   b) an electrical conductor formed at least partly on the planar member; and
   c) a gauge formed on the planar member and adapted to measure a physical effect on the planar member downhole, the physical effect being indicative of the group consisting of density and viscosity of a fluid in contact with the planar member while in a downhole environment;
   wherein said MEMS based reservoir fluid sensor is associated with a downhole tool operating within downhole conditions and wherein said sensor is capable of operating within downhole conditions.

2. The sensor of claim 1, wherein the planar member includes a movable element.

3. The sensor of claim 2, wherein the electrical conductor forms a conducting coil on the movable element.

4. The sensor of claim 3, further comprising a source of current adapted to supply an electrical current to the conducting coil and a magnetic field source being adapted to generate a magnetic field, the magnetic field and the electrical current interacting to generate a force on the movable element that causes the movable element to vibrate.

5. The sensor of claim 4, wherein the magnetic field source comprises an electromagnet formed on the planar member.

6. The sensor of claim 4, wherein the movable element comprises a plate that is attached to the substrate along one side.

7. The sensor of claim 6, wherein the gauge comprises a strain gauge positioned near the side where the plate attaches to the substrate.

8. The sensor of claim 4, wherein the gauge comprises a differential pressure gauge arranged to measure the differential pressure of an acoustic wave generated in the fluid by the vibrating movable element.

9. The sensor of claim 8, further comprising an absolute pressure gauge and a temperature gauge.

10. The sensor of claim 4, wherein the movable element comprises a plate that is attached to the substrate by two arms, a first arm extending from one side of the plate and a second arm extending from an opposing side.

11. The sensor of claim 10, wherein the gauge comprises a strain gauge positioned at least partially on the first arm.

12. The sensor of claim 11, wherein the electrical conductor traverses the second arm.

13. The sensor of claim 3, wherein the movable element comprises a plate that is attached to the substrate by a first plurality of arms extending from one side of the plate and by a second plurality of arms extending from an opposing side.

14. The sensor of claim 13, wherein the gauge comprises a strain gauge positioned at least partially on one of the first plurality of arms.

15. The sensor of claim 1, wherein the electrical conductor couples with a Wheatstone bridge formed on the planar member.

16. The sensor of claim 1, wherein the electrical conductor couples with a series of capacitors formed on the planar member.

17. The sensor of claim 1, wherein the gauge comprises a thermometer and the electrical conductor couples with a heater formed on the planar member.

18. The sensor of claim 1, wherein the substrate material is selected from the group consisting of: monocrystalline silicon, poly-silicon, and silicon carbide.

19. A MEMS based fluid sensor comprising:
a planar member machined from a substrate material;
a movable plate machined from the planar member and remaining partially attached to the planar member;
an electrically conducting coil formed on a surface of the movable plate;
at least one strain gauge positioned near where the movable plate remains attached to the planar member, and
means for determining a physical effect being indicative of the group consisting of density and viscosity of a fluid in contact with the movable plate while in a downhole environment;
wherein said MEMS based fluid sensor is associated with a downhole tool operating within downhole conditions and wherein said sensor is capable of operating within downhole conditions.

20. The sensor of claim 19, further comprising a magnetic field source adapted to generate a magnetic field approximately parallel or perpendicular to the surface of the movable plate.

21. The sensor of claim 19, wherein the movable plate comprises a flexural plate having four sides, the flexural plate being machined from the planar member along three sides and remaining attached to the planar member along one side.

22. The sensor of claim 19, wherein the movable plate comprises a plate attached to the planar member by at least two arms extending in opposite directions from the plate to the planar member.

23. A fluid sampling tool capable of operating within a downhole environment, said tool associated with a downhole tool and adapted to be moveable through a borehole that traverses an earth formation, comprising:
means for extracting a fluid from the earth formation into a container within the tool while downhole;
a Micro-Electro Mechanical Systems (MEMS) based sensor arranged to be in fluid contact with the fluid when held in the container in the downhole environment; and
means for activating the MEMS based sensor to measure a physical effect being indicative of the group consisting of density and viscosity of the fluid under down hole conditions.

24. The tool of claim 23, wherein the MEMS based sensor comprises:
a planar member machined from a substrate material;
an electrical conductor formed at least partly on the planar member; and
a gauge coupled with the planar member and adapted to measure the physical effect on the planar member, the physical effect being indicative of the group consisting of density and viscosity of the fluid.

25. A sample bottle capable of operating within a downhole environment and associated with a downhole tool and adapted to hold an oilfield reservoir fluid downhole comprising:
a container for holding the reservoir fluid; and
a Micro-Electro Mechanical Systems (MEMS) based sensor coupled to the container and arranged to be in fluid contact with the reservoir fluid in the downhole environment and held in the container for measuring a physical effect being indicative of the group consisting of density and viscosity of the reservoir fluid.

26. The sample bottle of claim 25, wherein the MEMS based sensor comprises:
a planar member machined from a substrate material;
an electrical conductor formed at least partly on the planar member; and
a gauge coupled with the planar member and adapted to measure the physical effect on the planar member, the physical effect being indicative of the group consisting of density and viscosity of the reservoir fluid.

27. The sample bottle of claim 25, further comprising a port adapted to receive the MEMS based sensor and through which the MEMS based sensor comes in contact with the reservoir fluid in the container.

28. A Micro-Electro Mechanical Systems (MEMS) based fluid sensor comprising:
a) a monolithic structure, machined from a substrate material, having a support portion allowing said monolithic structure to be attached to another structure, a plate portion capable of oscillating, and a flexible beam portion that decouples stress in said support portion from motion induced stress in said plate;
b) means for producing a magnetic field;
c) an electrical conductor, formed at least partly on said plate, allowing current flowing through said electrical conductor to interact with said magnetic field to induce oscillation of said plate;
d) a strain sensor, formed on said monolithic structure, adapted to detect movement of said plate downhole; and
e) means for determining a physical effect being indicative of the group consisting of density and viscosity of a fluid in contact with said plate in a downhole environment using said strain sensor detected plate movements;
wherein said MEMS based fluid sensor is associated with a downhole tool operating within downhole conditions and wherein said sensor is capable of operating within downhole conditions.

29. The sensor of claim 28, wherein said electrical strain sensor is selected from the group comprising a Wheatstone bridge, a back-EMF sensor, and an electrical impedance sensor.

30. The sensor of claim 28, wherein said means for producing a magnetic field is a permanent magnet positioned adjacent to but not in contact with said plate.

* * * * *